(12) United States Patent
Ruth et al.

(10) Patent No.: US 7,377,149 B2
(45) Date of Patent: May 27, 2008

(54) SENSOR

(75) Inventors: Juergen Ruth, Stuttgart (DE); Andreas Pesch, Krefeld (DE)

(73) Assignee: Robert Bosch GmbH, Stuttgart (DE)

( * ) Notice: Subject to any disclaimer, the term of this patent is extended or adjusted under 35 U.S.C. 154(b) by 93 days.

(21) Appl. No.: 10/547,400

(22) PCT Filed: Feb. 9, 2004

(86) PCT No.: PCT/DE2004/000215

§ 371 (c)(1),
(2), (4) Date: May 31, 2006

(87) PCT Pub. No.: WO2004/086023

PCT Pub. Date: Oct. 7, 2004

(65) Prior Publication Data

US 2007/0012087 A1    Jan. 18, 2007

(30) Foreign Application Priority Data

Mar. 27, 2003 (DE) ............................. 103 13 746
Oct. 14, 2003 (DE) ............................. 103 47 794
Jan. 22, 2004 (DE) ...................... 10 2004 003 187

(51) Int. Cl.
*G01N 27/407*  (2006.01)

(52) U.S. Cl. .................... 73/23.31; 73/31.05; 204/424; 204/426; 29/595

(58) Field of Classification Search ............... 73/23.31, 73/31.05; 204/421–429; 29/595
See application file for complete search history.

(56) References Cited

U.S. PATENT DOCUMENTS 6,231,348 B1 *  5/2001  Mayer et al. ................. 439/33
6,613,206 B1 *  9/2003  Weyl et al. .................. 204/424
2002/0029966 A1  3/2002  Nelson et al.
2002/0148280 A1 * 10/2002  Weyl et al. ................. 73/31.05
2003/0015020 A1 *  1/2003  Geier et al. ................. 73/23.31

FOREIGN PATENT DOCUMENTS

DE    195 23 911    1/1997

(Continued)

OTHER PUBLICATIONS

Patent Abstracts of Japan, vol. 2002, No. 11, Nov. 6, 2002 & JP 2002 202282 A (NGK Spark Plug Co Ltd.), Jul. 19, 2002, par. '0012.

*Primary Examiner*—Daniel S Larkin
(74) *Attorney, Agent, or Firm*—Kenyon & Kenyon LLP

(57) ABSTRACT

A measurement sensor for determining a physical property of a measurement gas, e.g., the concentration of a gas component or the temperature of a measurement gas, in particular of the exhaust gas of internal combustion engines, has a housing and a sensor element accommodated in the housing. The sensor element has an end segment at the measurement gas side that protrudes from the housing and a connection-side end segment that bears at least one contact surface. The sensor element also has at least one conductor element that contacts the at least one contact surface. In order to achieve low transition resistances at the electrical contacting and a decoupling from mechanical stress, the contact surface and the conductor element are connected to one another by welding, and are embedded in a ceramic compound at least in the area of the welded connection.

17 Claims, 2 Drawing Sheets

FOREIGN PATENT DOCUMENTS

| | | |
|---|---|---|
| DE | 195 42 650 | 5/1997 |
| DE | 101 32 828 | 1/2003 |
| EP | 0 624 791 | 11/1994 |
| EP | 0 704698 | 4/1996 |
| WO | WO 98/12549 | 3/1998 |
| WO | WO 03/005009 | 1/2003 |

* cited by examiner

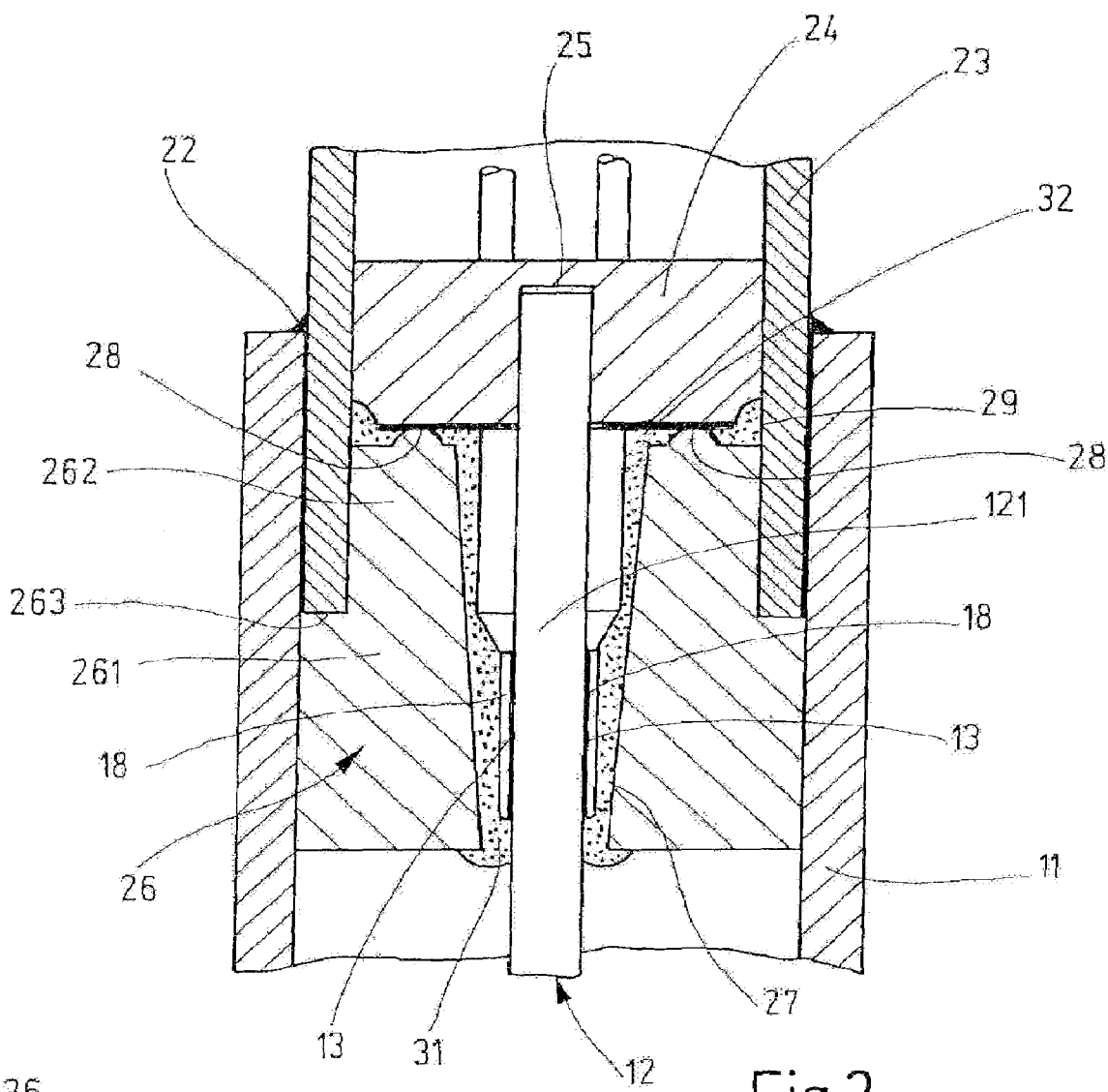
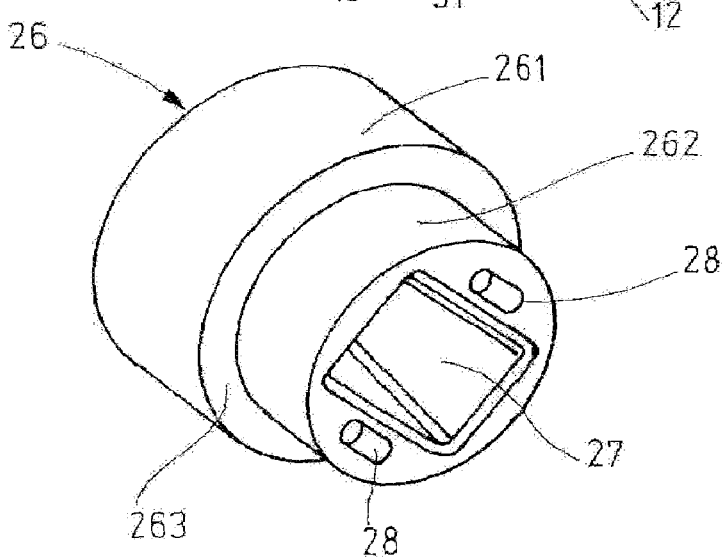

SENSOR

FIELD OF THE INVENTION

The present invention relates to a measurement sensor for determining a physical property of a measurement gas, e.g., the concentration of a gas component or the temperature of a measurement gas, e.g., of the exhaust gas of internal combustion engines.

BACKGROUND INFORMATION

In a known gas measurement sensor described, for example, in published German patent document DE 101 32 828, the contacting between the at least one contact surface and the at least one conductor element is created by a contact holder that uses a spring element to press the at least one conductor element onto the contact surface. The at least one conductor element is connected via a crimp connection to a connecting line with which the sensor element can be connected to an electronic control device, as described, for example, in published German patent document DE 195 42 650.

SUMMARY

The measurement sensor according to the present invention has the advantage that the welded connection ensures an optimal electrical transition impedance and enables economical manufacture. Through its embedding in an insulating ceramic compound, the welded connection is mechanically decoupled and is therefore not sensitive to vibrational stresses that can occur if the measurement sensor is used as an exhaust gas sensor in internal combustion engines in vehicles. As a result of the greater mechanical strength of the measurement sensor thus achieved, its useful life is significantly extended. The embedding can be achieved by pressing in or encapsulation with an insulating compound, or by a powder filling.

According to an example embodiment of the present invention, the ceramic compound is brought into the housing during the lining of the measurement sensor, as a compressed powder filling, and fills the space between the sensor element and the inner wall of the housing. Magnesium oxide (MgO) may be used as the powder material. For the pressing in or encapsulating, a ceramic casting compound may be used. Alternatively, ceramic glue, steatite, or aluminum oxide ($Al_2O_3$) can also be used.

According to an example embodiment of the present invention, the welded connection is created by resistance welding. The welding of the conductor element, which may be made of nickel (Ni), to the contact surface, e.g., made of platinum or a platinum cermet, can however also be carried out using a welding laser.

According to an example embodiment of the present invention, a counter disk that spans the housing cross-section is fixed in the housing, and the at least one conductor is led through this counter disk. A sealing piece that fills the housing cross-section and that has a feedthrough that surrounds the sensor element in the area of the welded connection is pressed into the housing, and the intermediate space between the counter disk and the sealing piece, as well as between the sensor element and the wall of the feedthrough, is filled completely with a ceramic casting compound and/or a ceramic glue. This example embodiment has the advantage that even given a miniaturization of the measurement sensor the addition of the ceramic casting compound or of the ceramic glue results in an optimal insulating binding of the welded connection and an optimal gas-tight sealing of the sensor element. Here the introduction of the ceramic casting compound or of the ceramic glue is very simple, because the position of the filling support does not have to be very precise. The ceramic casting compound or the ceramic glue can be filled with a high tolerance as to quantity, because when the sealing piece is pushed in via the feedthrough in the sealing piece, excess compound is pressed out of the intermediate space between the sealing piece and the counter disk, and can be removed at the exposed end of the sealing piece if necessary. The quality of the seal can also be assessed on the basis of the quantity of ceramic casting compound or ceramic glue exiting the feedthrough. Because the ceramic casting compound or the ceramic glue both seals the welded connection to the sealing piece and also seals the intermediate space between the sealing piece and the counter disk to the housing, the conventional sealing packing of two steatite disks with a boron nitride disk situated between them can be omitted, so that a construction of the measurement sensor that is short in the axial direction may be achieved. However, such a sealing system is to be provided in the cases in which the sensor element is to be additionally held, for example in order to avoid vibrational movements of the sensor element.

According to an example embodiment of the present invention, the feedthrough provided in the sealing piece for the sensor element has in the area of the welded connection an inner cross-section that is matched to the cross-sectional shape of the sensor element, the inner cross-section decreasing continuously as it extends from the end surface facing the counter disk to the end surface of the sealing piece facing away from the counter disk. In the distribution of the ceramic casting compound and/or of the ceramic glue brought about by pushing in the sealing piece, this tapering of the feedthrough has a throttling effect, so that the ceramic casting compound or ceramic glue is first distributed radially in uniform fashion, and is then increasingly pressed out through the feedthrough as the sealing piece is pressed further in.

The pre-assembly of the measurement sensor for creating the gas-tight routing of the at least one conductor connected to the sensor element out of the housing takes place in the following method steps:

The counter disk through which the at least one conductor element is led is fixed in the housing, the sealing piece is placed on the sensor element, the end of the sensor element is inserted into the blind hole of the counter disk, and the at least one conductor element protruding from the counter disk is welded to a contact surface on the sensor element. A determined quantity of ceramic casting compound and/or ceramic glue is now dispensed onto the counter disk, and the sealing piece on the sensor element is pushed towards the counter disk until between the end surface of the sealing piece and the counter disk there remains only a small intermediate space, whose minimum axial depth is determined by the spacer piece provided on the sealing piece. In this intermediate space between the sealing piece and the counter disk, the ceramic casting compound or the ceramic glue seals the sealing piece and counter disk against the housing. The blind hole of the counter disk has a through hole to the cable harness.

BRIEF DESCRIPTION OF THE DRAWINGS

FIG. 2 shows a cross-sectional view of a segment of a longitudinal section of the measurement sensor according to a second exemplary embodiment.

FIG. 3 shows a perspective view of a sealing piece of the measurement sensor shown in FIG. 2.

DETAILED DESCRIPTION

Figure 1:
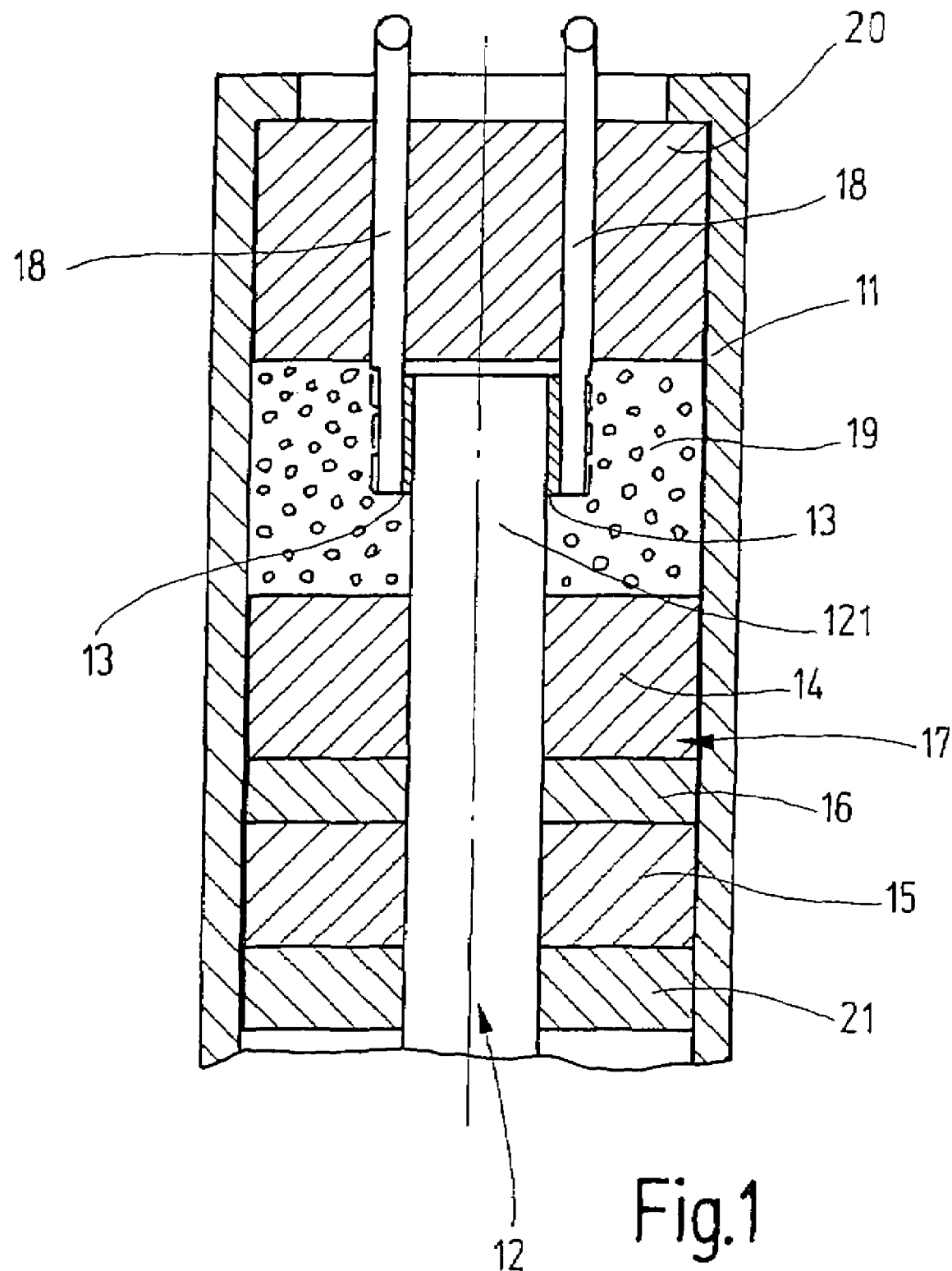
FIG. 1 shows a cross-sectional view of a segment of a longitudinal section of a measurement sensor.

The measurement sensor according to the present invention, of which a segment is shown in longitudinal section in FIG. 1, is used to determine a physical property of a measurement gas.

Such a property is for example the concentration of a gas component or the temperature of the measurement gas. As an example, this measurement sensor is used in internal combustion engines in vehicles as an exhaust gas sensor that measures either the concentration of oxygen in the exhaust gas of the internal combustion engine (lambda sensor) or the temperature of the exhaust gas (temperature sensor).

The measurement sensor has a housing 11 that accommodates a sensor element 12 that protrudes with a measurement-gas-side end segment from housing 11 and is exposed to the measurement gas. On an end segment 121 at the connection side, sensor element 12 has, on surfaces facing away from one another, a plurality of contact surfaces 13 made of platinum or of a platinum cermet that are connected to electrical printed conductors (not shown here) that lead to the measurement-gas-side end segment. In the exemplary embodiment, two of these contact surfaces 13 are shown. Sensor element 12 is led through a sealing system 17 that is situated between the two end segments and that supports sensor element 12 on housing 11 and mechanically dampens its vibrations, as well as sealing connection-side end segment 121 against the measurement gas. Sealing system 17 is made of two ceramic shaped parts 14 and 15, e.g., made of steatite, that clamp between them a sealing element 16, made, e.g., of boron nitride.

For connecting sensor element 12 to an electronic control device, each contact surface 13 is contacted by a conductor element 1 that is routed to a connecting plug that is connected to the connecting line to the electronic control device, as described, for example, in published German patent document DE 195 23 911. Conductor element 18 may be made of nickel (Ni). In order to create an electrical contact with minimal transition impedances, conductor elements 18 are welded to their allocated contact surfaces 13; resistance welding may be used as a welding method, but laser welding can also be used.

In the installation of sensor element 12 in housing 11, in the area of the welded connections, sensor element 12 is embedded in a ceramic compound 19 that surrounds the connection-side end segment 121 of sensor element 12 and is supported on the inner wall of housing 11. In the exemplary embodiment, the embedding is made in a compressed, high-temperature-resistant powder filling that completely fills the space between the connection-side end segment 121 of sensor element 12 and the inner wall of housing 11 up to sealing system 17. As a powder, magnesium oxide (MgO) may be used. However, the embedding in ceramic compound 19 can also take place through encapsulation or pressing in. In this case, a ceramic casting compound, a ceramic glue, or steatite or aluminum oxide ($Al_2O_3$) is used as a material.

Ceramic compound 19 is covered at one end of the housing by an insulating disk 20 that is supported peripherally on the inner wall of housing 11, through which conductor elements 18 are led. Insulating disk 20 may be made of aluminum oxide. At its end, housing 11 is crimped onto insulating disk 20, so that insulating disk 20 is axially fixed. On the side of sealing system 17 facing the measurement-gas-side end segment, an additional insulating disk 21 is situated that surrounds sensor element 12 and lies peripherally against the inner wall of housing 11.

Because insulating ceramic compound 19 also has a sealing function and seals connection-side end segment 121 of sensor element 12 against the exhaust gas, in the case in which ceramic compound 19 is not the described powder filling but rather a press compound or casting compound, sealing system 17 can be realized in simplified fashion, for example, by omitting components 15 and 16 of sealing system 17.

According to another exemplary embodiment, the measurement sensor of which a segment is shown in longitudinal section in FIG. 2 has a housing 11 into one end of which a tube-shaped, possibly flexible connecting piece 23 is pushed, in which conductor elements 18 are led to a connecting plug that terminates connecting piece 23. A counter disk 24 is placed into connecting piece 23 with an axial distance from the tube end penetrating into housing 11 of this connecting piece, and conductor elements 18 are led through this counter disk. As in the exemplary embodiment of FIG. 1, conductor elements 18 are fixed electrically and mechanically by a welded connection to contact surfaces 13 that are present on large surfaces, facing away from one another, of connection-side end segment 121 of sensor element 12. Counter disk 24 has a central blind hole (recess) 25, open towards the interior of the housing, whose inner cross-section corresponds to the cross-section of sensor element 12, so that the end of sensor element 12 is able to penetrate into blind hole 25 so as to form a positive fit with only a small gap spacing. Blind hole 25 has a through bore (not shown) through which connection-side end segment 121 of sensor element 12 is connected to the surrounding atmosphere. Housing 11 and connecting piece 23 are connected to one another by a weld seam 22 or a circumferential caulking.

A sealing piece 26 that has a central feedthrough 27 and that fills the inner cross-section of housing 11 is placed into housing 11. Cylindrical sealing piece 26 has two cylinder segments 261, 262 having different diameters. With its cylindrical segment 262 having the smaller diameter, sealing piece 26 is pushed without a gap into the tubular segment of connecting piece 23 that penetrates into housing 11, and its larger-diameter cylindrical segment 261 presses against the inner wall of housing 11. On its end surface facing counter disk 24, sealing piece 26 has two spacing elements 28 that are supported on counter disk 24, so that in the inserted state of sealing piece 26, as shown in FIG. 2, it is ensured that only a minimal intermediate space 29 remains between counter disk 24 and smaller-diameter cylindrical segment 262. In this inserted state of sealing piece 26, feedthrough 27 surrounds sensor element 12 in the area of contact surfaces 13 and conductor elements 18, which are welded to contact surfaces 13. As is shown in FIG. 2 and FIG. 3, the inner cross-section of feedthrough 27 is matched to the shape of sensor element 12, and in this exemplary embodiment is rectangular. Feedthrough 27 tapers, beginning from the end surface of sealing piece 26 facing counter disk 24, towards the end surface of sealing piece 26 facing away from counter disk 24.

The assembly of the measurement sensor for creating the gas-tight extension of conductor elements 18 out of housing 11 is carried out with the following method steps:

Connecting piece 23 (which may be a protective tube) with inserted counter disk 24 and conductor elements 18 led through it is completely pre-assembled. Sensor element 12 is inserted into blind hole 25 of counter disk 24, and conductor elements 18 protruding from counter disk 24 are welded to contact surfaces 13 on sensor element 12. Sensor element 12 and connecting piece 23 are placed into housing 11, and housing 11 and connecting piece 23 are welded to one another. Next, a determined quantity of ceramic casting compound 31 (alternatively, ceramic glue 31) is dispensed into connecting piece 23, onto counter disk 24. Then sealing piece 26, pushed onto sensor element 12, is pushed into the tube end of connecting piece 23 with its smaller-diameter cylindrical segment 262. The insertion pressure first results in a uniform radial distribution of ceramic casting compound 31 in the intermediate space 29 between sealing piece 26 and counter disk 24. When intermediate space 29 is maximally filled, ceramic casting compound 31 increasingly enters into feedthrough 27, and, as a result of the throttle effect of the tapered feedthrough 27, is finally pressed out from feedthrough 27 as the press-in pressure increases, at the end side of sealing piece 26 facing away from counter disk 24. The pushing of sealing piece 26 into connecting piece 23 is terminated as soon as annular shoulder 263 formed between cylindrical segments 261, 262 runs into the annular end surface of connecting piece 23, or at the latest when spacing elements 28 come into contact with counter disk 24. In order to prevent the penetration of ceramic casting compound 31 into the gap that remains between blind hole 25 in counter disk 24 and sensor element 12, a sealing element 32, which tightly surrounds sensor element 12, is placed on the end surface of counter disk 24 facing sealing piece 26. Sealing element 32 can for example be a small, round fiberglass matting that is slit in the penetration area of sensor element 12. If there is a risk that ceramic casting compound 31 will dry out due to its consistency, sealing piece 26 is assembled in the wet state.

What is claimed is:

1. A measurement sensor for determining a physical property of a measurement gas, comprising:
    a housing;
    a sensor element accommodated in the housing, wherein a first end segment of the sensor element on a first side is configured to be exposed to the measurement gas by protruding from the housing, and wherein a second end segment of the sensor element on a second side has at least one contact surface; and
    at least one conductor element that contacts the at least one contact surface;
    wherein:
        the at least one contact surface and the at least one conductor element are connected to each other by welding;
        at least in an area of welded connection, the at least one contact surface and the at least one conductor element are embedded in an insulating ceramic compound; and
        the insulating ceramic compound fills a space that extends from an inner wall of the housing to the second end segment of the sensor element.

2. The measurement sensor as recited in claim 1, wherein the physical property includes one of a concentration of a component of the measurement gas and a temperature of the measurement gas, and wherein the welded connection between the at least one contact surface and the at least one conductor element is formed by one of resistance welding and laser welding.

3. The measurement sensor as recited in claim 1, wherein the at least one contact surface is made of one of platinum and a platinum cermet.

4. The measurement sensor as recited in claim 1, wherein the at least one conductor element is made of nickel.

5. The measurement sensor as recited in claim 1, wherein the insulating ceramic compound includes a compressed powder filling that fills the space between the inner wall of the housing and the second end segment of the sensor element, and wherein the compressed powder filling includes magnesium oxide.

6. The measurement sensor as recited in claim 1, wherein the at least one contact surface and the at least one conductor element are embedded in the insulating ceramic compound by pressing in the ceramic compound, and wherein the insulating ceramic compound includes one of a ceramic casting compound, a ceramic glue, steatite, and aluminum oxide.

7. The measurement sensor as recited in claim 6, further comprising:
    a counter disk fixed in the housing, wherein the at least one conductor element extends through the counter disk;
    a sealing piece that is pressed into the housing and that fills at least a portion of the inner space of the housing, wherein the sealing piece has a feed-through channel that surrounds the sensor element in the area of welded connection between the at least one contact surface and the at least one conductor element; and
    at least one of a ceramic casting compound and a ceramic glue filling: a) an intervening space between the counter disk and the sealing piece; and b) an intervening space between the sensor element and a wall defining the feed-through channel.

8. The measurement sensor as recited in claim 7, wherein the feed-through channel has a cross-section shape that is substantially matched to a cross-section shape of the sensor element, and wherein the cross-section of the feed-through channel tapers toward an end of the sealing piece facing away from the counter disk.

9. The measurement sensor as recited in claim 7, wherein the counter disk has a recess that receives the sensor element with a positive fit.

10. The measurement sensor as recited in claim 7, wherein an end surface of the sealing piece facing the counter disk has at least one axially protruding spacer element for supporting the sealing piece on the counter disk.

11. The measurement sensor as recited in claim 7, further comprising:
    a tubular connecting piece fixedly connected to the housing, wherein one end of the tubular connecting piece penetrating into the housing;
    wherein the counter disk is positioned within the tubular connecting piece at a distance from the one end of the tubular connecting piece, and wherein at least a segment of the sealing piece is pressed into the one end of the tubular connecting piece.

12. The measurement sensor as recited in claim 7, wherein a further sealing element is provided on an end surface of the counter disk facing the sealing piece, and wherein the further sealing element also surrounds the sensor element.

13. The measurement sensor as recited in claim 1, wherein a first end surface of the insulating ceramic compound on the second side is covered by a terminating disk that is supported peripherally on an inner wall of the housing, and wherein the at least one conductor element extends through the terminating disk.

14. The measurement sensor as recited in claim 13, wherein the housing is crimped onto the terminating disk.

15. The measurement sensor as recited in claim 1, wherein a second end surface of the insulating ceramic compound is juxtaposed by a sealing system that surrounds the sensor element, and wherein the sealing system is supported in a gas-tight manner on an inner wall of the housing.

16. The measurement sensor as recited in claim 15, further comprising:
   an additional insulating disk provided on an end of the sealing system facing away from the insulating ceramic compound, wherein the additional insulating disk surrounds the sensor element and is supported on the housing.

17. A method for assembling a measurement sensor, the measurement sensor including: a housing; a sensor element accommodated in the housing and having at least one contact surface; at least one conductor element that contacts the at least one contact surface, wherein the at least one contact surface and the at least one conductor element are connected to each other by welding, and wherein, at least in an area of welded connection, the at least one contact surface and the at least one conductor element are embedded in an insulating ceramic compound; a counter disk fixed in the housing, wherein the at least one conductor element extends through the counter disk, and wherein the counter disk has a recess that receives the sensor element; a sealing piece that is pressed into the housing and that fills at least a portion of the inner space of the housing, wherein the sealing piece has a feed-through channel that surrounds the sensor element in the area of welded connection between the at least one contact surface and the at least one conductor element, and wherein an end surface of the sealing piece facing the counter disk has at least one axially protruding spacer element; and at least one of a ceramic casting compound and a ceramic glue filling a) an intervening space between the counter disk and the sealing piece, and b) an intervening space between the sensor element and a wall defining the feed-through channel; the method comprising:
   fixing the counter disk in the housing, wherein the at least one conductor element extends through the counter disk;
   inserting the sensor element into the recess of the counter disk;
   welding the at least one conductor element to the at least one contact surface;
   dispensing a quantity of at least one of the ceramic casting compound and the ceramic glue onto the counter disk that is fixed in the housing; and
   pressing the sealing piece into the housing towards the counter disk to the extent that the intervening space between the counter disk and the sealing piece is filled with the at least one of the ceramic casting compound and the ceramic glue, wherein a minimum axial depth of the intervening space between the counter disk and the sealing piece is determined by the at least one axially protruding spacer element.

* * * * *